(12) United States Patent  (10) Patent No.: US 8,641,605 B2
Shoroji et al.  (45) Date of Patent: Feb. 4, 2014

(54) ENDOSCOPE

(75) Inventors: Ayanori Shoroji, Hino (JP); Katsushi Watanabe, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1683 days.

(21) Appl. No.: 11/821,645

(22) Filed: Jun. 25, 2007

(65) Prior Publication Data

US 2008/0009677 A1 Jan. 10, 2008

(30) Foreign Application Priority Data

Jul. 4, 2006 (JP) ................................. 2006-184784

(51) Int. Cl.
*A61B 1/06* (2006.01)
(52) U.S. Cl.
USPC ........................................................ 600/178
(58) Field of Classification Search
USPC ................. 600/101, 131, 153, 156, 178, 179; 348/68, 73
See application file for complete search history.

(56) References Cited

U.S. PATENT DOCUMENTS

| 6,221,007 | B1* | 4/2001 | Green | 600/160 |
| 6,315,712 | B1* | 11/2001 | Rovegno | 600/109 |
| 6,692,432 | B1* | 2/2004 | Yarush et al. | 600/179 |
| 7,214,183 | B2* | 5/2007 | Miyake | 600/131 |
| 2002/0022769 | A1 | 2/2002 | Smith et al. | |
| 2002/0087047 | A1* | 7/2002 | Remijan et al. | 600/109 |
| 2003/0163025 | A1* | 8/2003 | Kaji | 600/132 |
| 2004/0133075 | A1* | 7/2004 | Motoki et al. | 600/131 |
| 2004/0204628 | A1* | 10/2004 | Rovegno | 600/131 |
| 2005/0222499 | A1* | 10/2005 | Banik et al. | 600/132 |
| 2006/0004258 | A1* | 1/2006 | Sun et al. | 600/160 |
| 2006/0155168 | A1* | 7/2006 | Pease | 600/131 |
| 2006/0173242 | A1* | 8/2006 | Navok et al. | 600/133 |
| 2006/0183977 | A1* | 8/2006 | Ishigami et al. | 600/179 |
| 2006/0276689 | A1* | 12/2006 | Litscher et al. | 600/156 |
| 2007/0123752 | A1* | 5/2007 | Melanson | 600/182 |

FOREIGN PATENT DOCUMENTS

| JP | 63-502728 | 10/1988 |
| JP | 09-187414 | 7/1997 |
| JP | 09-285443 | 11/1997 |
| JP | 11-009548 | 1/1999 |
| JP | 2000-112953 | 4/2000 |
| JP | 2002-177197 | 6/2002 |
| JP | 2002-288978 | 10/2002 |
| JP | 2005-084192 | 3/2005 |
| JP | 2005-101779 | 4/2005 |
| JP | 2005-192739 | 7/2005 |
| JP | 2005-204886 | 8/2005 |
| WO | WO 87/04913 | 8/1987 |
| WO | WO 2004/041096 | 5/2004 |

* cited by examiner

*Primary Examiner* — Philip R Smith

(74) *Attorney, Agent, or Firm* — Scully, Scott, Murphy & Presser, P.C.

(57) ABSTRACT

An endoscope of the invention includes: an LED for supplying illumination light to illuminate a subject; an image pickup device for picking up an image of a region to be inspected of the subject; a video display device provided with a monitor portion on which an endoscope image of the region to be inspected picked up by the image pickup device is displayed and an exterior member for holding the monitor portion; a power supply control circuit for supplying electric power to drive the LED and cause the LED to emit illumination light; and a heat radiation portion for radiating heat generated by the power supply control circuit formed on a rear surface opposing to a disposition surface of the exterior member on which the monitor portion of the video display device is provided.

8 Claims, 10 Drawing Sheets

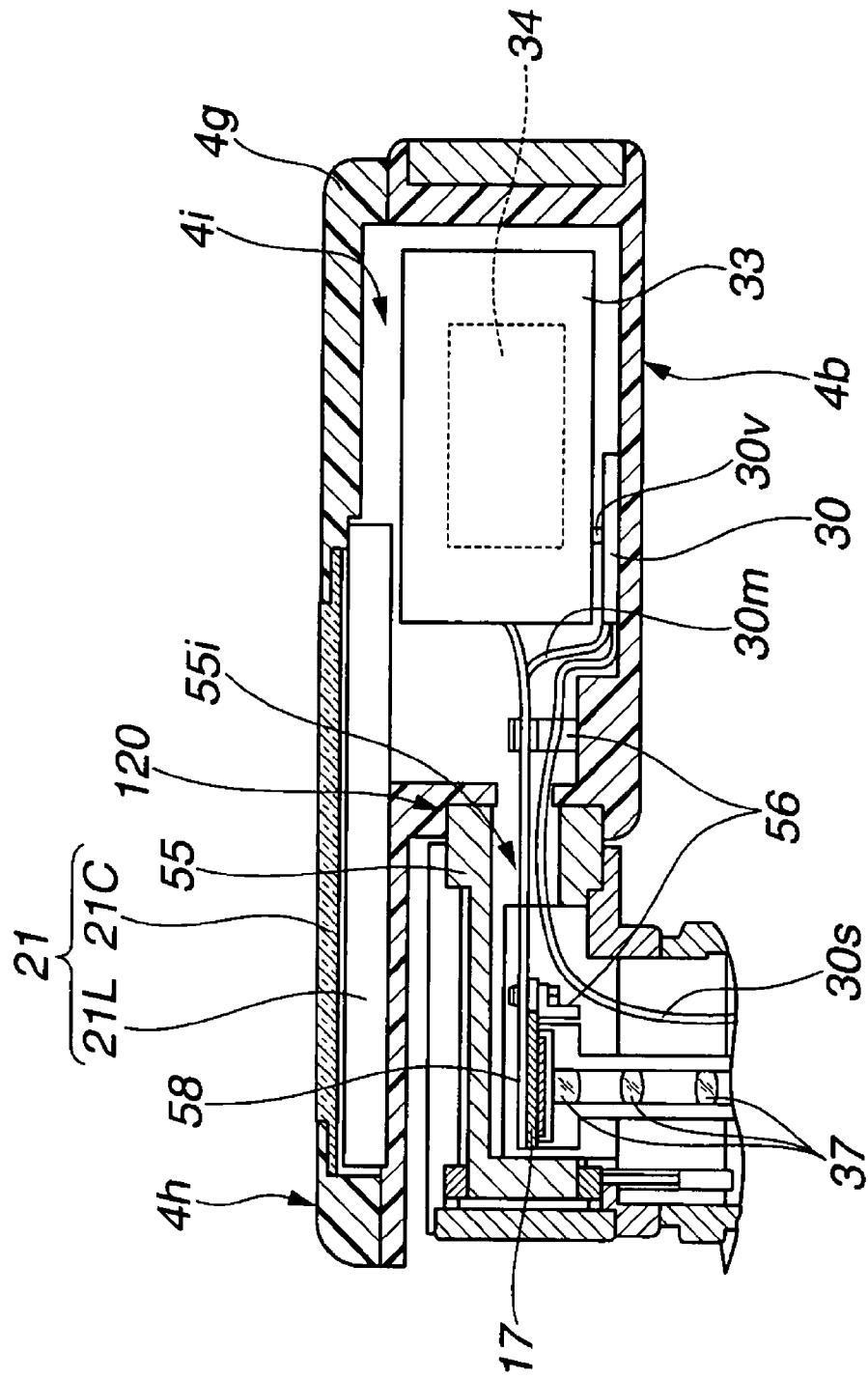

ENDOSCOPE

CROSS REFERENCE TO RELATED ART

This application claims the benefit of Japanese Application No. 2006-184784 filed in Japan on Jul. 4, 2006, the contents of which are incorporated herein by this reference.

BACKGROUND OF THE INVENTION

1. Field of the Invention

The present invention relates to an endoscope including an operation portion to which a display device for displaying an endoscope image picked up by image pickup portion is connected.

2. Description of Related Art

Conventionally, as a light source of an endoscope, well-known is a light source lamp built in a light source device as a peripheral device to which an endoscope is connected. When illumination light is supplied to an endoscope from a light source device, the illumination light emitted from a light source lamp is transmitted to a distal end of an insertion portion via from a universal cord to an operation portion of the endoscope, by means of light guide fiber extended inside of the endoscope, and then the illumination light is irradiated from the distal end of the insertion portion to a region to be inspected.

In addition, in recent years, for the purpose of simplifying a whole endoscope apparatus including an endoscope and peripheral devices, well-known is an endoscope having a configuration in which a light source is configured of a light emitting diode provided in the endoscope and a display device for displaying an endoscope image is connected to an operation portion.

Providing a light source configured of the light emitting diode in the endoscope eliminates the need for a light source device connected to the endoscope, thereby simplifying the endoscope apparatus. In addition, the light emitting diode is capable of emitting light with lower electric power compared with light source lamp and the like, thereby realizing power saving in the endoscope apparatus. Furthermore, connecting the display device to the operation portion eliminates the need for a monitor device to be separately connected to the endoscope, thereby simplifying the endoscope apparatus.

In addition, in the endoscope, also provided is a light emitting diode driving circuit which is a light source driving circuit for applying electric power supplied from a battery provided to the display device, for example, to the light emitting diode after adjusting the electric power to the current rating of the light emitting diode.

Incidentally, an endoscope generally has watertight structure, since the outer surface of the endoscope is cleaned after use. That is, inside of the endoscope except for an opening of a duct and the like, is occluded by an exterior member. In order to reduce the weight of the whole endoscope, the exterior member of the endoscope is usually made of plastic material.

However, if the light emitting diode emits light, and in addition, the light emitting diode driving circuit continues to be driven, for example, in an enclosed space inside the operation portion in the endoscope covered with the plastic exterior member, there is a problem such that the light emitting diode is degraded by heat radiated in the enclosed space inside the operation portion due to the light emission of the light emitting diode and the driving of the light emitting diode driving circuit, and the lifetime of the light emitting diode is shortened, since the plastic exterior member has a low heat transfer efficiency.

Therefore, conventionally, there has been a compelling circumstance to make the light emitting diode emit light with electric power lower than the rated value in consideration of heat radiation efficiency of the plastic exterior member and the lifetime of the light emitting diode.

In view of such a circumstance, Japanese Unexamined Patent Application Publication No. 9-285443 discloses an endoscope having a configuration in which a small size illumination lamp as a light source is provided in a distal end portion of an insertion portion of the endoscope, and a light emission control circuit serving as a light source driving circuit for supplying electric power to the small size illumination lamp is provided in an operation portion of the endoscope. With such a configuration, the small size illumination lamp and the light emission control circuit are provided in different spaces, so that a heat radiating position from the small size illumination lamp and a heat radiating position from the light emission control circuit are different. Therefore, in the configuration, heat radiation points are dispersed, so that heat is radiated from the whole endoscope, while preventing localized heat radiation.

In addition, Japanese Unexamined Patent Application Publication No. 2002-112953 discloses a light source device which is mounted to a light source mounting port of an operation portion of an endoscope, and the light source has such a configuration that an LED lamp as a light source and a constant current source as a light source driving circuit are disposed separately from each other. With such a configuration, a heat radiating position from the LED lamp and a heat radiating position from the constant current source are different, thereby preventing localized heat radiation.

SUMMARY OF THE INVENTION

Briefly, an endoscope of the present invention comprises: an elongated insertion portion inserted into a subject; an operation portion provided in a linked manner on a proximal end side of the insertion portion; illumination portion for supplying illumination light for illuminating the subject, the illumination portion being provided in the insertion portion or in the operation portion; image pickup portion for picking up an image of a region to be inspected of the subject, the image pickup portion being provided in the insertion portion or in the operation portion; a display device including a display portion on which an endoscope image of the region to be inspected picked up by the image pickup portion is displayed and a frame body for holding the display portion, the display device being connected to the operation portion; a light source driving circuit for supplying electric power to drive the illumination portion and cause the illumination portion to emit illumination light, the light source driving circuit being provided in one of the insertion portion, the operation portion, and the display device; and a heat radiation portion for radiating heat generated from the light source driving circuit, the heat radiation portion being formed on a rear surface opposing to a disposition surface of the frame body on which the display portion in the display device is disposed.

The above and other objects, features and advantages of the invention will become more clearly understood from the following description referring to the accompanying drawings.

BRIEF DESCRIPTION OF THE DRAWINGS

FIG. 10 is a cross-sectional view showing a modification example of internal configurations of a part of the operation portion and the video display device.

DETAILED DESCRIPTION OF PREFERRED EMBODIMENTS

Hereinafter, an embodiment of the present invention will be described with reference to the drawings. Note that, an endoscope will be described taking a medical endoscope as an example in the embodiment below.

Figure 1:
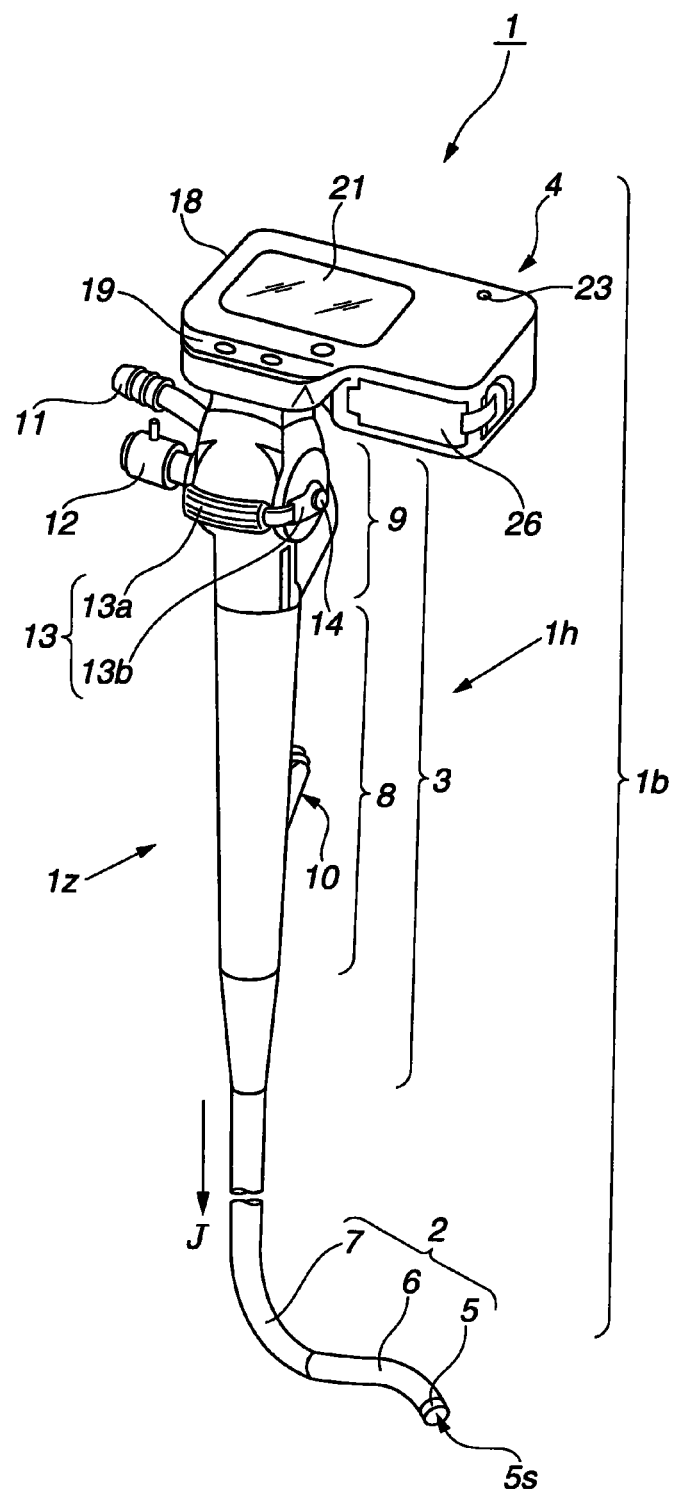
FIG. 1 is a perspective view showing an endoscope according to an embodiment of the present invention.
Figure 2:
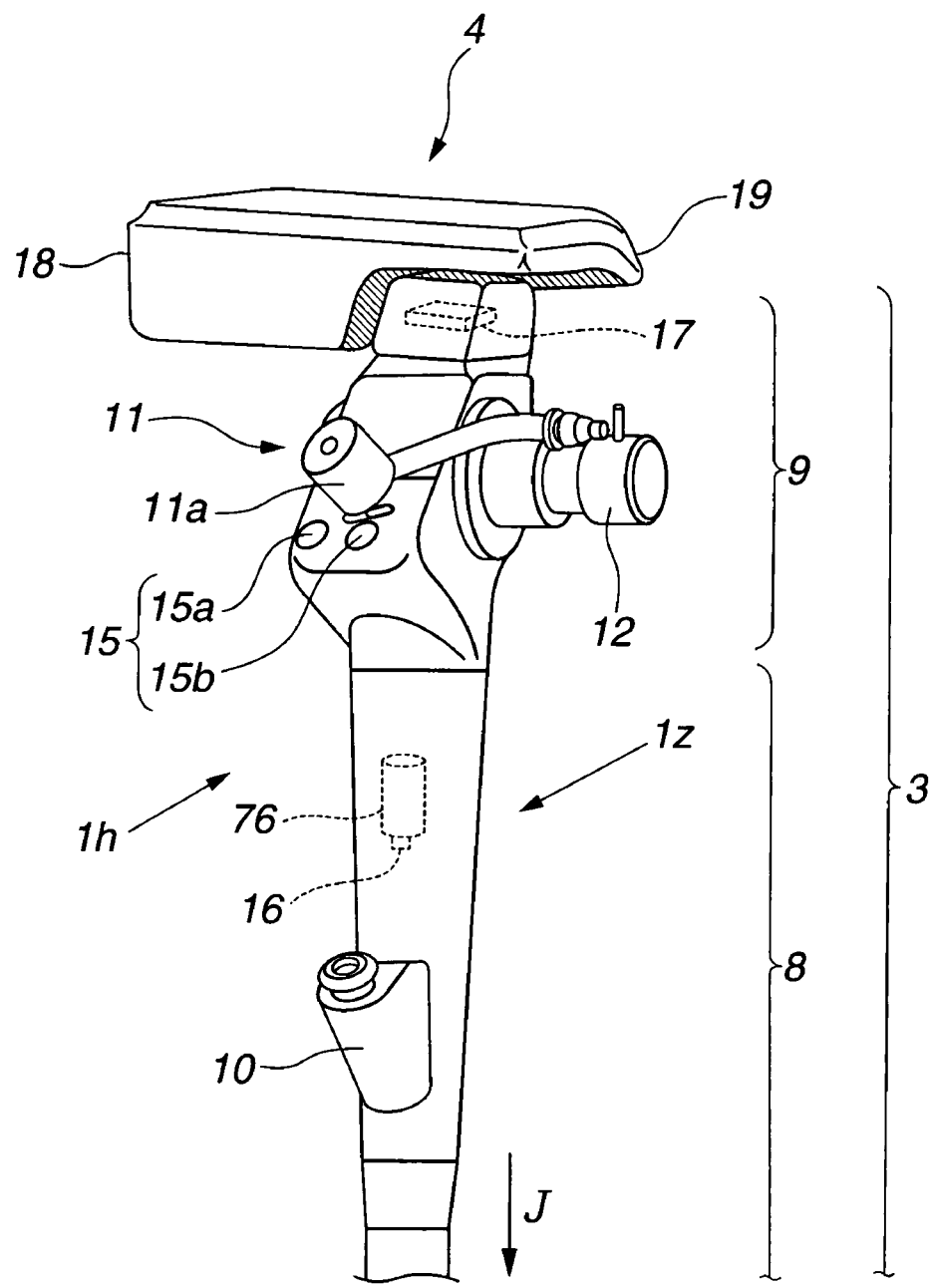
FIG. 2 is a partial perspective view showing the endoscope in FIG. 1 viewed from a rear surface side in FIG. 1.
Figure 3:
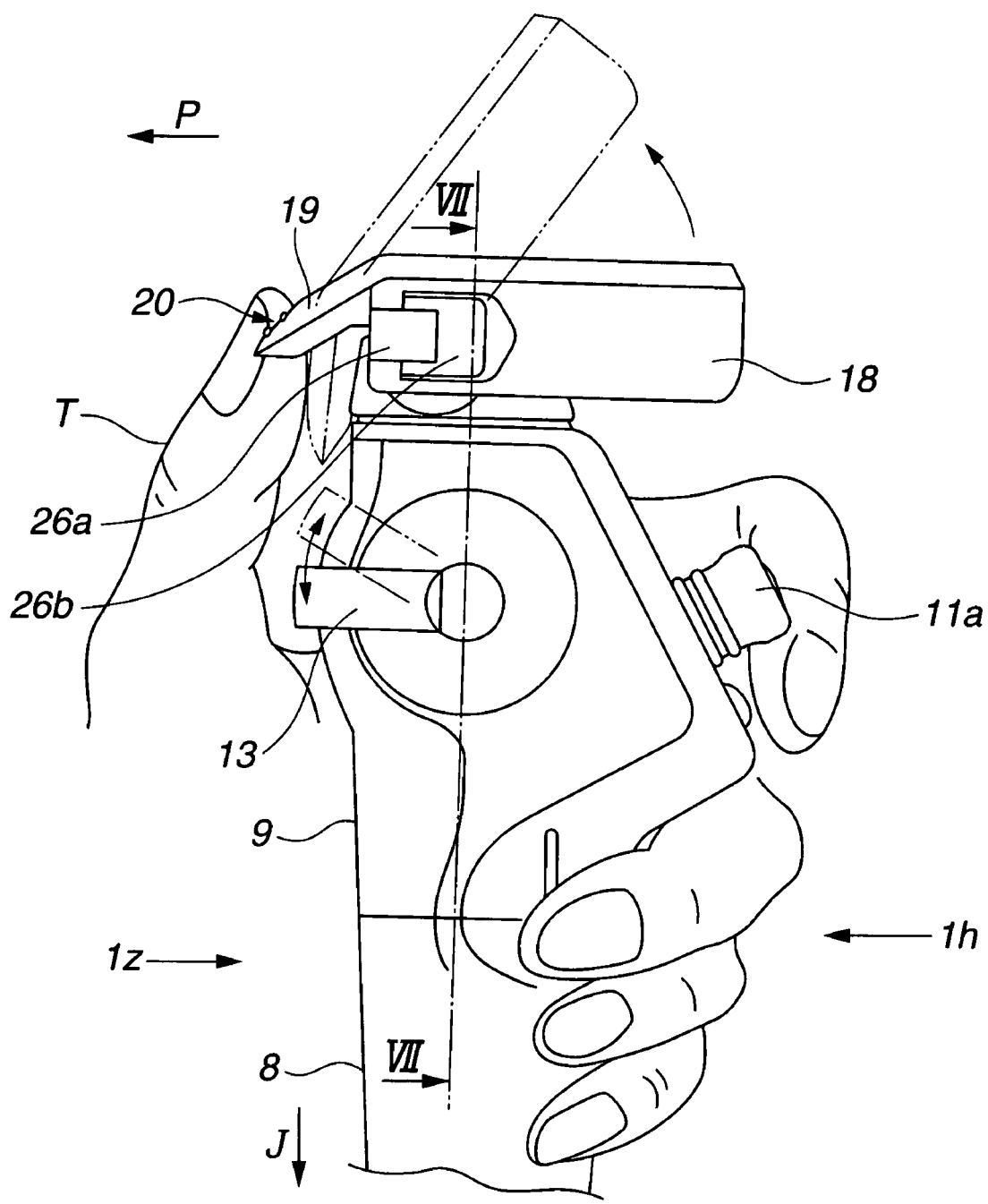
FIG. 3 is a partially enlarged plan view showing a state where a video display device of the endoscope in FIG. 1 is rotatable.
Figure 4:
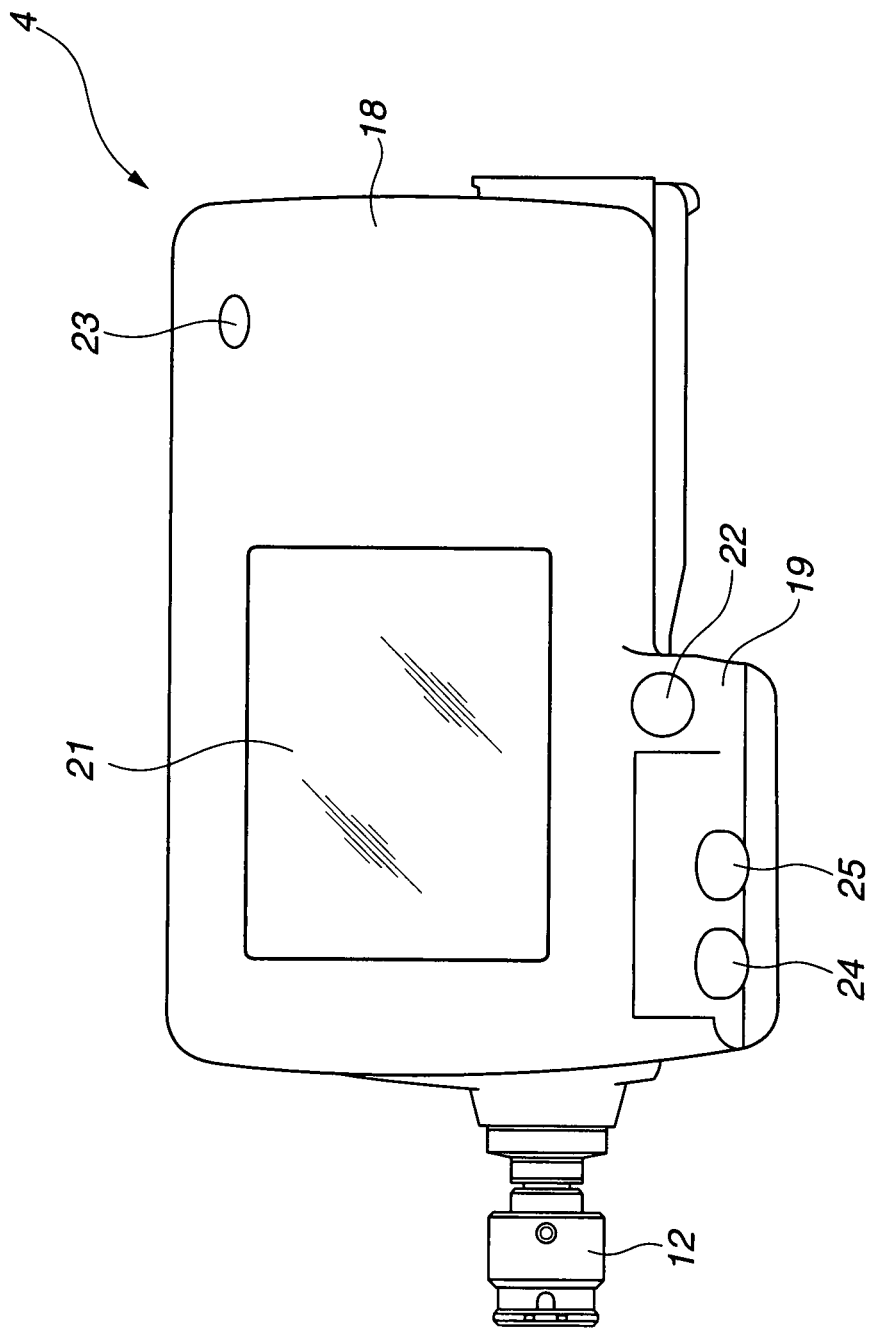
FIG. 4 is a plan view of the video display device of the endoscope in FIG. 1.

FIG. 1 is a perspective view showing an endoscope according to an embodiment of the present invention, FIG. 2 is a partial perspective view showing the endoscope in FIG. 1 viewed from a rear surface side in FIG. 1, FIG. 3 is a partially enlarged plan view showing a state where a video display device of the endoscope in FIG. 1 is rotatable, and FIG. 4 is a plan view of the video display device of the endoscope in FIG. 1.

As shown in FIG. 1, an endoscope main body 1b of an endoscope 1 has a main part configured of an insertion portion 2 inserted into a region to be inspected in a body cavity as a subject, an operation portion 3 provided in a linked manner on a proximal end side of the insertion portion 2, and a video display device 4 which is a display device connected to an upper end of the operation portion 3.

The insertion portion 2 is formed to be flexible in an elongated shape, and has a main part configured of a rigid distal end portion 5 located on a distal end side thereof, a bending portion 6 provided in a linked manner on a proximal end side of the distal end portion 5, and a flexible portion 7 provided in a linked manner on a proximal end side of the bending portion 6.

The operation portion 3 has a main part configured of a grasping portion 8 to be grasped by an operator when the operator grasps the endoscope 1, and an operation portion main body 9 provided on a proximal end side of the grasping portion 8.

The grasping portion 8 has an exterior formed in a shape such that an operator can grip with the thumb T (see FIG. 3) and the other fingers of his or her left hand, for example in a bar-like shape. Note that the grasping portion 8 may be formed in a shape such that the operator can grip with his or her right hand.

In addition, the grasping portion 8 includes, on a rear surface 1h side of the endoscope 1, a treatment instrument insertion port 10 for inserting and withdrawing a treatment instrument into and from a body cavity by inserting and withdrawing the treatment instrument such as a forceps through the suction duct 100 to be described later (see FIGS. 5 and 6) which is extended inside the endoscope 1.

As shown in FIG. 2, the operation portion main body 9 has, on the rear surface 1h side of the endoscope 1, a suction base 11 used for sucking liquid such as body fluid and phlegm from the body cavity.

Figure 6:
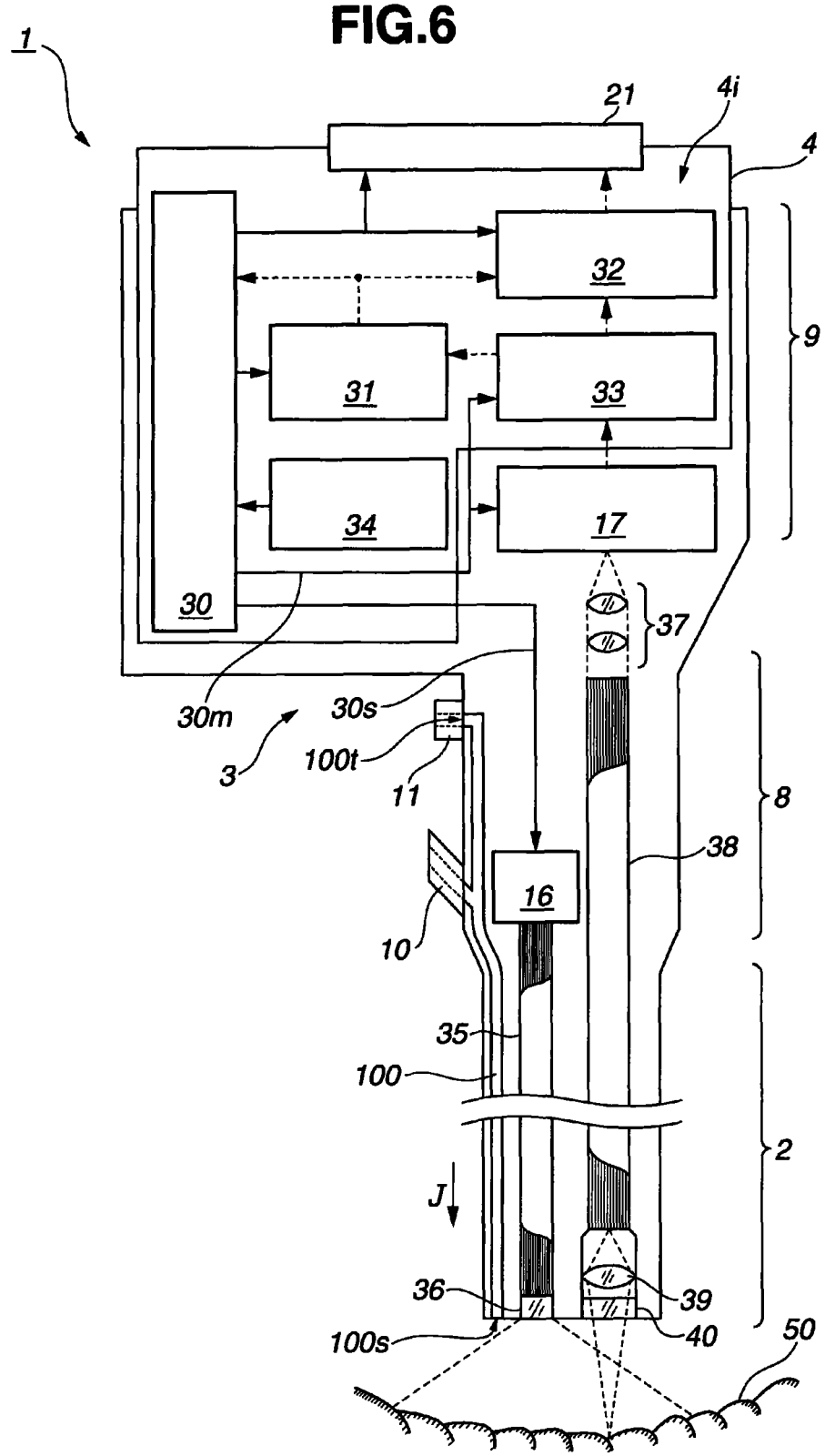
FIG. 6 is a view schematically showing an internal configuration of endoscope in FIG. 1, mainly illustrating an image pickup system and an illumination optical system.

To the suction base 11, a suction device is connectable via a tube not shown. An operator activates the suction device and operates a suction button 11a (see FIG. 2) to be described later, and thereby the operator can cause the suction device to suck body fluid, phlegm and the like from the body cavity via the suction duct 100 which is a fluid duct extended in the operation portion 3 and the insertion portion 2 such that one end 100t is opened at the operation portion main body 9 and the other end 100s is opened on a distal end surface 5s of the distal end portion 5, as shown in FIG. 6 to be described later.

Note that a tube may be inserted into a flow path in the suction duct 100, and via the tube, an insufflation device for insufflating air into the body cavity may be connectable to the suction base 11 communicating with inside of the tube.

In addition, the operation portion main body 9 has on the left side in FIG. 1 a vent base 12 for insufflating air into the insertion portion 2 and the operation portion 3 in performing a leakage inspection of the endoscope 1.

To the vent base 12, an air-feeding device is connectable via a tube not shown. The operator activates the air-feeding device and feeds air in water into the endoscope 1 from the vent base 12, thereby allowing a leakage inspection of the endoscope 1.

Furthermore, to the vent base 12, a cap and the like, not shown, for releasing air from inside of the endoscope 1 is detachably provided such that a part of the endoscope 1, for example, a rubber, not shown, covering an outer circumference of the distal end portion 5 does not burst due to negative pressure when the endoscope 1 is left under negative pressure environment, for example, a sterilization processing or a transportation by air.

Figure 5:
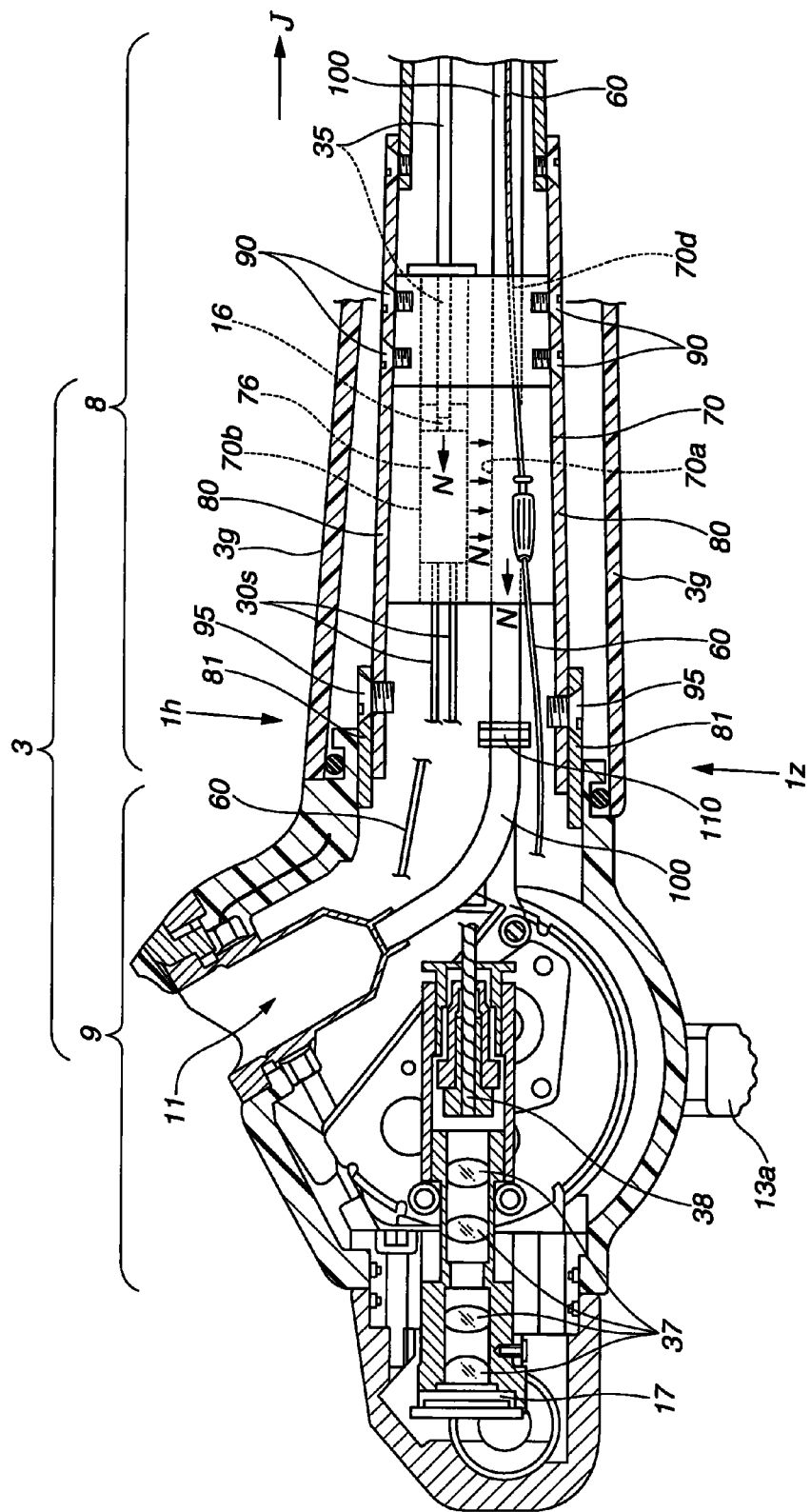
FIG. 5 is a partially enlarged cross-sectional view schematically showing an internal configuration of an operation portion of the endoscope in FIG. 1.

In addition, the operation portion main body 9 has, on a front surface 1z side of the endoscope 1, a bending operation lever 13 for bending a bending portion 6 in for example up and down directions, through a bending operation wire 60 (see FIG. 5).

The bending operation wire 60 is extended in the insertion portion 2 and the operation portion 3, with one end fixed to a distal end of a bending piece not shown in the bending portion 6 or to the distal end portion 5, and the other end fixed to a pulley and the like, not shown, provided in the operation portion 3.

The bending operation lever 13 is provided at a position adjacent to the grasping portion 8 such that the operator can operate the lever with the thumb T of the left hand gripping the grasping portion 8. In addition, the bending operation lever 13 has an L shape formed by a finger-hooking portion 13a provided to the operation portion main body 9 on the front surface 1z side of the endoscope 1 and an arm portion 13b provided in a linked manner to the finger-hooking portion 13a.

In the bending operation lever 13, the finger-hooking portion 13a is provided at a predetermined position of the operation portion main body 9 with the arm portion 13b rotatably pivoted to the rotational shaft 14 passing through the operation portion main body 9 in the right and left direction in FIG. 1.

Furthermore, as shown in FIG. 2, the operation portion main body 9 has, on the rear surface 1h side of the endoscope 1, an image switch 15 configured of an image recording switch 15a and an image reproduction switch 15b. The image recording switch 15a is turned on when recording a video displayed on the video display device 4 into a recording medium of a recording control circuit 31 to be described later (see FIG. 6), and the image reproduction switch 15b is turned on when reproducing the recorded image.

In addition, the above-described suction button 11a is provided to the operation portion main body 9 so as to be positioned on the rear surface 1h side of the endoscope 1 and in the vicinity of the image switch 15.

In the grasping portion 8, for example, a white light emitting diode (hereinafter referred to as LED) 16, which is illuminating means configuring an illumination portion for supplying illumination light to illuminate a subject, is provided by means to be described later. In addition, in the operation portion main body 9, there is disposed an image pickup device 17 configured of CCD, CMOS, or the like serving as image pickup means configuring an image pickup portion for picking up an image of the region to be inspected.

The video display device 4 has an outer shape formed by a boxy device main body 18 of approximately rectangular parallelepiped shape, and a tilt lever 19 serving as the finger-hooking portion extended to the front surface 1z side of the endoscope 1 so as to form a plane from a corner portion of one side of the device main body 18.

On an upper surface of the device main body 18 configuring a disposition surface 4h of an exterior member 4g to be described later (as for both of these, see FIGS. 7 and 9) of the video display device 4, provided are a monitor portion 21 as a display portion for displaying an endoscope image picked up by the image pickup device 17, a power display lamp 23 to be turned on when the power is turned on, and a power switch 22 for turning on and off a power source of the endoscope main body 1b, as shown in FIG. 4.

Furthermore, on an upper surface of the tilt lever 19 configuring the disposition surface 4h of the exterior member 4g of the video display device 4, provided are a still image recording changeover switch 24 and a moving image recording changeover switch 25. The still image recording switch 24 is turned on when setting the endoscope image to be recorded as a still image, and the moving image changeover switch 25 is turned on when setting the endoscope image to be recorded as a moving image.

Note that, the still image recording changeover switch 24 and the moving image recording changeover switch 25 may be provided on the upper surface of the device main body 18. Also, the power switch 22 may be provided on the upper surface of the tilt lever 19.

In addition, on the upper surface of the device main body 18 or the tilt lever 19, the above-described image recording switch 15a and the image reproduction switch 15b may be provided.

As shown in FIG. 1, the device main body 18 has on a surface of the front surface 1z side of the endoscope 1 an openable/closable lid body 26 for containing and detaching a battery 34 and a memory medium such as a memory card, not shown, into and from a containing portion not shown.

The components disposed in the device main body 18 have watertight structure, and the openable/closable lid body 26, in particular, includes a fixing nail 26a and a buckle lever 26b to obtain secure watertight structure with respect to the containing portion of the device main body 18.

The video display device 4 is configured such that, in a connecting portion 120 to be described later (see FIG. 7) between the device main body 18 and the operation portion main body 9, the monitor portion 21 is rotatable, as shown in FIG. 3, between a position where the display surface of the monitor portion faces the upper direction in the drawing which is an insertion axis direction J of the insertion portion 2 and a position where the display surface of the monitor portion faces the front surface 1z side of the endoscope 1 which is a direction P approximately orthogonal to the insertion axis direction, by means of a rotational shaft 55 to be described later provided penetrating in right/left direction in FIG. 1.

The video display device 4 is rotated by rotating the tilt lever 19 by a cushion of the thumb T of the left hand of the operator gripping the grasping portion 8, for example. Note that a plurality of slip stoppers 20 as convex portions (see FIG. 3) are formed on the upper surface of the tilt lever 19.

Next, a configuration in which the LED 16 is disposed in the operation portion 3 will be described with reference to FIG. 5. FIG. 5 is a partially enlarged cross-sectional view schematically showing an internal configuration of the operation portion of the endoscope in FIG. 1.

As shown in FIG. 5, inside of the grasping portion 8 of the operation portion 3, which is watertightly occluded by an exterior member 3g, metal frames 80, which are plate-like heat transfer frames formed in a semi-cylinder shape, are extendedly provided so as to face each other in the insertion axis direction J along the exterior member 3g on the front surface 1z side and the rear surface 1h side of the endoscope 1. Each of the metal frames 80 is respectively fixed with a screw 95 to each of interposing plates 81 fixed to the inner surface of the exterior member 3g.

In addition, in a space between the metal frames 80 facing each other, the suction duct 100, an image guide 38, the bending operation wire 60, and a light guide bundle 35 formed by biding light guide fibers are extendedly provided, and in addition, a cable 30s extended from a power supply control circuit 30 (see FIG. 6) to be described later to the LED 16 is provided in order to transmit the electric power supplied from the battery 34 to the LED 16.

Furthermore, in the space between the metal frames 80 facing each other, an illumination means fixing member 70 serving as an illumination portion fixing member is fixed with screws 90 serving as mounting members.

Note that the illumination means fixing member has been conventionally used as a member for fixing the bending operation wire 60 by butting a coil covered on an outer circumference of the bending operation wire 60 against the member. The illumination means fixing member 70 according to the present embodiment is formed larger than the conventionally employed illumination means fixing member.

The illumination means fixing member 70 is formed with a solid and approximate cylinder-shaped member, as shown in FIG. 5, and is made of heat transfer member such as aluminum or brass, for example. In addition, the illumination means fixing member 70 includes through holes 70a to 70e (through holes 70c and 70e are not shown) formed along the insertion axis direction J. Note that, in the illumination means fixing member 70, only a portion between the through holes 70a and 70b may be formed of the heat transfer member.

The through hole 70a configures a fluid duct insertion hole of the present invention, and the suction duct 100 which is a fluid duct extended in the grasping portion 8 is inserted into the through hole 70a such that a part of the suction duct 100 closely contacts the inner circumference of the through hole 70a.

The through hole 70b configures an illumination means disposing space serving as an illumination portion disposing space of the present invention, and an LED base 76 to be described later, the light guide bundle 35, and the cable 30s are inserted into the through hole 70b.

To be concrete, the LED base 76 made of metal, to which the LED 16 is fixed such that the LED 16 butts against one end surface of the light guide bundle 35, is inserted into the through hole 70b. Note that, on the LED base 76, a substrate and the like not shown, to which an end portion of the cable 30s is connected, are disposed. In addition, the LED base 76 is fixed so as to closely contact the inner circumference of the through hole 70b.

The through hole 70c has the image guide 38 inserted therethtough. The through holes 70d, 70e have the bending operation wire 60 inserted therethrough, with the above-described coil of the bending operation wire 60 butted thereagainst.

Next, description will be made on the internal configuration of the endoscope 1 which is mainly configured by the image pickup system and the illumination optical system, with reference to FIGS. 6 to 9. FIG. 6 is a view schematically showing an internal configuration of the endoscope in FIG. 1, mainly illustrating an image pickup system and an illumination optical system, and FIG. 7 is a cross-sectional view of a part of the operation portion and a video display device taken along the VII-VII line of FIG. 3.

Figure 7:
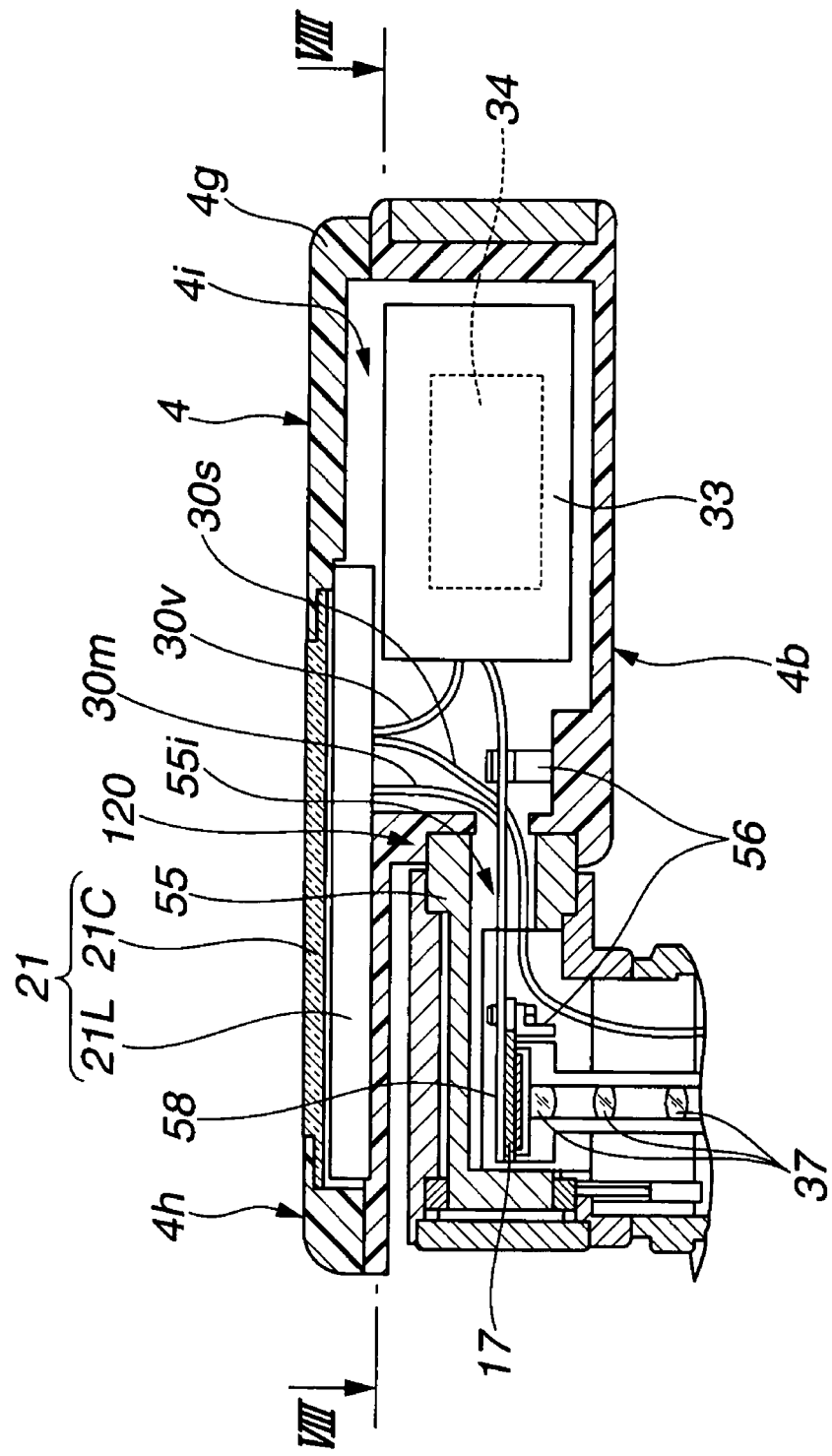
FIG. 7 is a cross-sectional view of a part of the operation portion and a video display device taken along the VII-VII line of FIG. 3.
Figure 8:
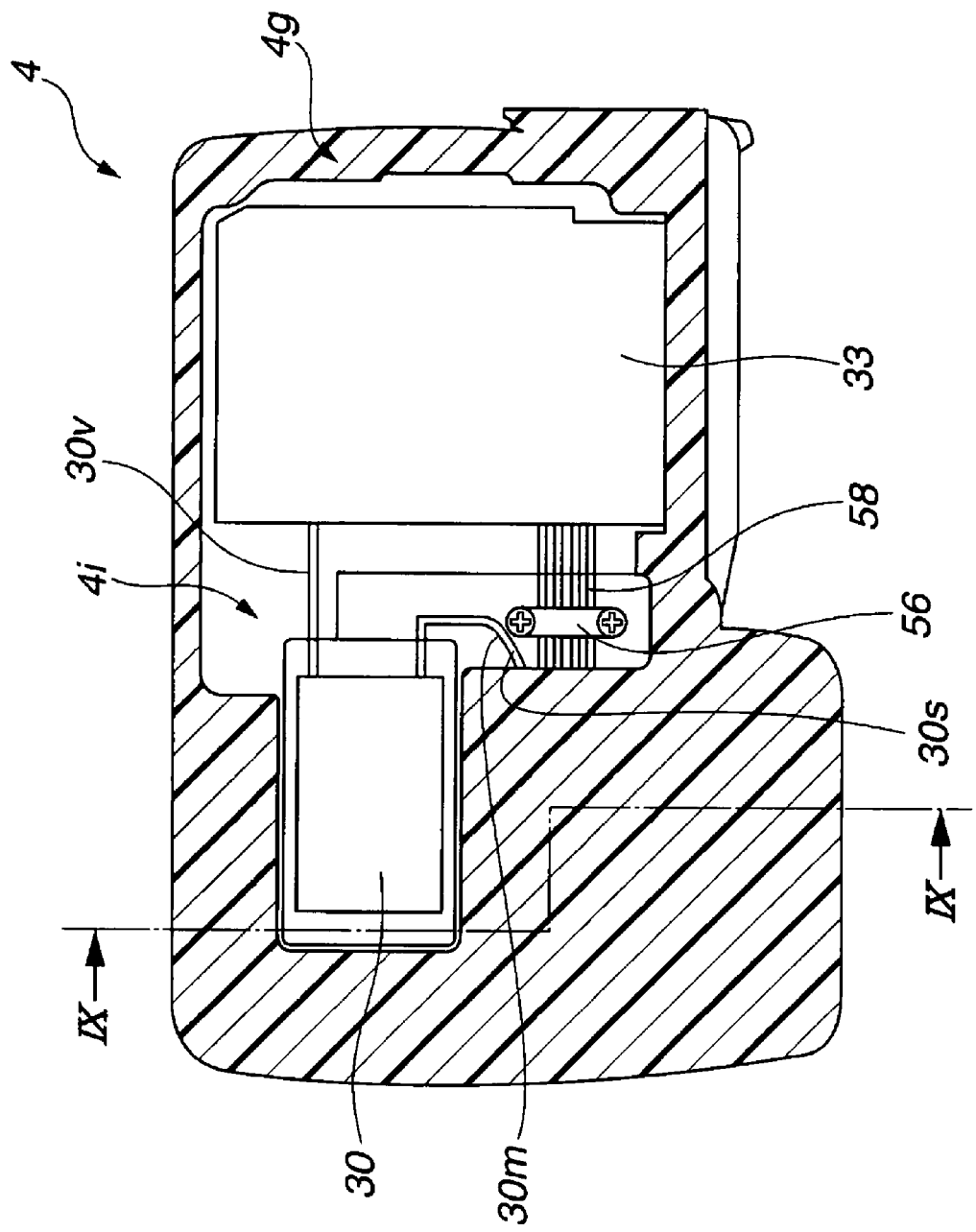
FIG. 8 is a cross-sectional view of the video display device taken along the VIII-VIII line of FIG. 7.
Figure 9:
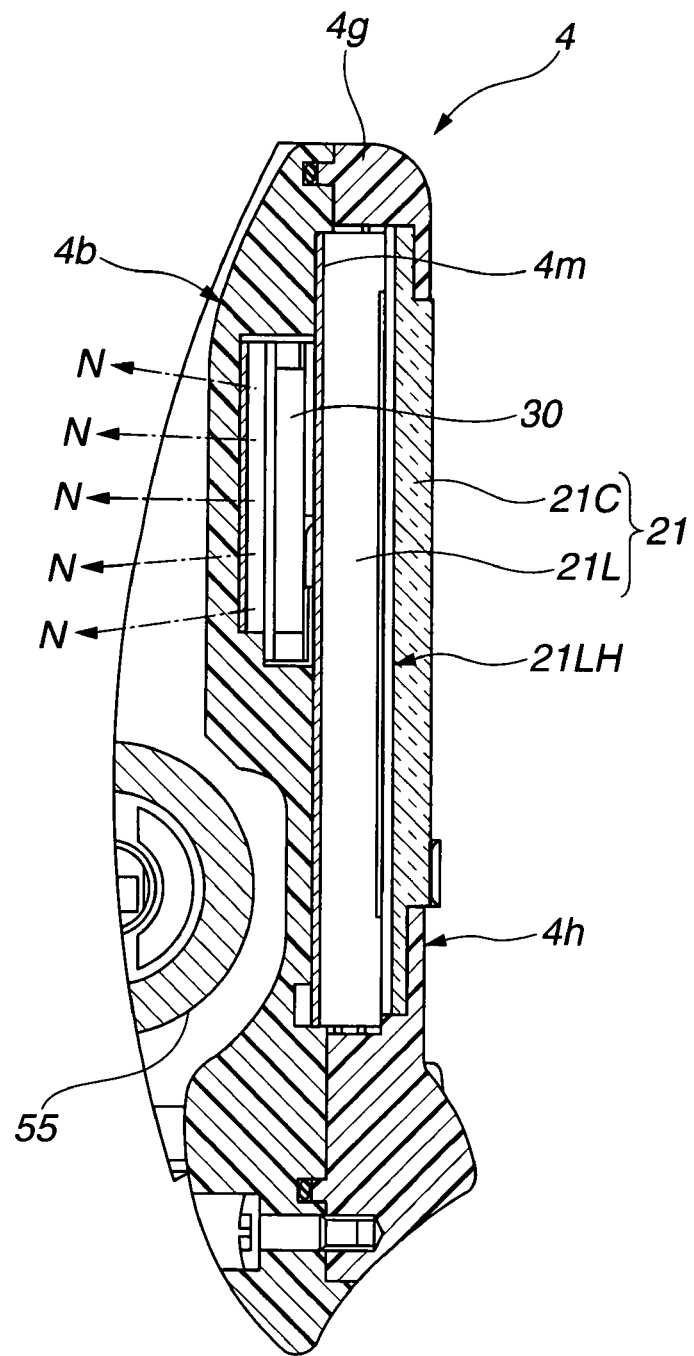
FIG. 9 is a cross-sectional view of the video display device taken along the IX-IX line of FIG. 8.

FIG. 8 is a cross-sectional view of the video display device taken along the VIII-VIII line of FIG. 7, and FIG. 9 is a cross-sectional view of the video display device taken along the IX-IX line of FIG. 8.

As shown in FIG. 6, in an interior portion 4i watertightly occluded by the exterior member 4g serving as a frame body of the video display device 4, in addition to the above-described monitor portion 21 and the battery 34, provided are the power supply control circuit 30 serving as the light source driving circuit, the recording control circuit 31 serving as recording means configuring a recording section, a display device control circuit 32, and an image pickup device control circuit 33 serving as image pickup means configuring an image pickup section.

On the disposition surface 4h of the exterior member 4g of the video display device 4, a depression 4m having a concave shape is formed such that the size of the plane is approximately equal to that of the above-described monitor portion 21, as shown in FIG. 9.

The depression 4m has fitted thereinto a display device such as a liquid crystal display (hereinafter referred to as an LCD) 21L which is a display member and a transparent cover member 21C which covers a display surface 21LH of the LCD 21L. Note that the LCD 21L and the cover member 21C configure the monitor portion 21. That is, the exterior member 4g holds the monitor portion 21.

Furthermore, as shown in FIG. 6, the above-described light guide bundle 35 and the image guide 38 are extended from the insertion portion 2 to the grasping portion 8 of the operation portion 3 inside the endoscope 1.

From the distal end portion 5 to the operation portion main body 9, the above-described suction duct 100 is extended, and in addition, from the bending portion 6 to the operation portion main body 9, the above-described bending operation wire 60 (not shown in FIG. 6) is extended.

Illumination light from the LED 16 provided in the grasping portion 8 is irradiated on the one end surface of the light guide bundle 35 positioned so as to butt against the LED 16.

Then, the illumination light is transmitted from the one end surface of the light guide bundle 35 to the other end surface thereof positioned at the distal end portion 5, and thereafter, irradiated from an illumination lens 36 provided on a distal end side of the other end surface of the light guide bundle 35 on a predetermined range in a direction of region to be inspected 50 in the body cavity.

A reflected light image from the region to be inspected 50 to which the illumination light is irradiated is transmitted to one end of the image guide 38 after being incident on the other end of the image guide 38 via an image pickup lens 40 and an objective lens 39 provided to the distal end portion 5. After that, the reflected light image led from the one end of the image guide 38 goes through a condenser lens 37 provided in the operation portion main body 9 to be formed on the image pickup device 17.

As shown in FIG. 9, the power supply control circuit 30 is provided in the interior portion 4i of the video display device 4 so as to be positioned in a plane space on a side closer to a rear surface 4b of the exterior member 4g than the monitor portion 21 but not to contact the rear surface 4b. Note that the rear surface 4b of the exterior member 4g configures a heat radiation portion for radiating heat generated by the power supply control circuit 30.

The power supply control circuit 30 receives the electric power supplied from the battery 34 to output corresponding driving powers to the LED 16, the image pickup device 17, the monitor portion 21, the recording control circuit 31, the display device control circuit 32, and the image pickup device control circuit 33, respectively.

Note that the driving electric powers are outputted to the image pickup device 17 and the LED 16 provided in the operation portion 3, via the cables 30s, 30m inserted in the space 55i in the metal rotational shaft 55 in the connecting portion 120 between the operation portion 3 and the video display device 4, as shown in FIGS. 7 and 8. Since the cables 30s, 30m are inserted in the space 55i in the metal rotational shaft 55, radiation noises from the cables 30s, 30m are shielded by the rotational shaft 55.

The driving electric powers are outputted to the recording control circuit 31, the display device control circuit 32, and the image pickup device control circuit 33, in the interior portion 4i of the video display device 4, via a cable 30v.

The power supply control circuit 30 is configured to include the above-described power switch 22, and turned on and off by the power switch 22. Note that the battery 34 is configured of a secondary battery which can be repeatedly used by charging.

The image of the region to be inspected 50 picked up by the image pickup device 17 is outputted from the image pickup device 17 to the image pickup device control circuit 33 via an image pickup cable 58 having one end connected to the image pickup device 17 and the other end connected to the image pickup device control circuit 33.

Note that, also the image pickup cable 58 is inserted in the space 55i in the rotational shaft 55 in the connecting portion 120. In addition, the image pickup cable 58 has a middle part held by a pair of cramp members 56 provided so as to face each other in the vicinity of the rotational shaft 55 in the operation portion main body 9 and the video display device 4, as shown in FIG. 7 to prevent the connection by soldering with the image pickup device 17 and the image pickup device control circuit 33 from detaching, even if the image pickup cable 58 is twisted by the rotational movement of the video display device 4.

The image pickup device control circuit 33 converts the image of the region to be inspected 50 picked up by the image pickup device 17 into a signal to output the signal to the recording control circuit 31 and the display device control circuit 32.

A recording medium such as an XD picture card is detachably attached to the recording control circuit 31. To the recording control circuit 31, supplied are input signals from the image switch 15 (see FIG. 2) provided in the operation portion main body 9, and the still image recording changeover switch 24 and the moving image recording changeover switch 25 provided in the video display device 4 (as for both of the switches, see FIG. 1).

In response to the input signals from these various kinds of switches, the recording control circuit 31 performs controls such as recording the signal of the endoscope image as a still image or a moving image, and reproducing and stopping the recorded image. That is, the recording control circuit 31 stores in a recording medium the image of the region to be inspected 50 converted into a signal by the image pickup device control circuit 33, and outputs the stored signal to the display device control circuit 32 in response to instruction signals such as reproduction and stop by the image reproduction switch 15b.

The display device control circuit 32 visualizes the signal from the recording control circuit 31 or the image pickup device control circuit 33 to cause the monitor portion 21 to display the endoscope image. In addition, the recording control circuit 31, in response to the signals inputted from the various kinds of switches 15, 24, and 25, feeds to the power supply control circuit 30 an instruction signal for supplying electric power to the LED 16, the image pickup device 17, and image pickup device control circuit 33.

In the endoscope 1 configured as such, when the power switch 22 is turned on, electric power is supplied from the power supply control circuit 30 of the video display device 4. After the display device 4 of the endoscope 1 is activated in an image reproduction mode, an image recorded in the recording control circuit 31 is displayed on the monitor potion 21. Note that, in this state, electric power is not supplied to the LED 16 and the image pickup device 17 from the power supply control circuit 30.

After that, when the operator turns on the still image recording changeover switch 24 and the video display device 4 of the endoscope 1 becomes a still image recording standby state, electric power is supplied also to the LED 16 and the image pickup device 17 from the power supply control circuit 30. This allows the image under observation to be transmitted from the image pickup device 17 in the following order to the image pickup device control circuit 33, the display device control circuit 32, and the monitor portion 21, to be displayed in real time on the monitor portion 21.

In a case of recording a still image in this state, if the operator turns on the image recording switch 15a, an image signal is inputted to the recording control circuit 31 from the image pickup device control circuit 33, and the still image is recorded in an internal memory as a recording medium of the recording control circuit 31. Note that, after the recording, the image under observation is automatically displayed again on the monitor portion 21.

After that, when the operator turns on the image reproduction switch 15b, an image signal is outputted to the display device control circuit 32 from the recording control circuit 31, and the recorded still image is displayed on the monitor portion 21. Then, when the operator turns off the image reproduction switch 15b, the image under observation is displayed on the monitor portion 21 instead of the still image.

In addition, if the operator turns on the moving image recording changeover switch 25 in this state, the video display device 4 of the endoscope 1 becomes a moving image recording standby state. Also in this case, the image under observation is transmitted from the image pickup device 17 in the following order to the image pickup device control circuit 33, the display device control circuit 32, and the monitor portion 21 to be displayed in real time on the monitor portion 21.

In a case of recording a moving image in this state, if the operator turns on the image recording switch 15a, the moving image is recorded in the internal memory of the recording control circuit 31 similarly as described above.

During the recording of the moving image, either the image pickup device control circuit 33 or the recording control circuit 31 outputs the image signal in real time to the display device control circuit 32, and the image under observation is displayed in real time on the monitor portion 21.

After that, if the operator turns off the image recording switch 15a, the recording is stopped, and the image under observation is displayed on the monitor portion 21 instead of the moving image. In a case of reproducing the moving image subsequently, if the operator turns on the image reproduction switch 15b, a control of moving image reproduction is performed similarly as that of the still image reproduction. When the moving image reproduction is finished, similar control of when the above-described still image reproduction is finished is performed, and thereafter the video display device 4 of the endoscope 1 returns to the state at the time of the activation.

Next, actions of the present embodiment configured as such will be described. Note that, the following description will be made on the actions of the heat radiation methods of the LED 16 in the operation portion 3 and of the power supply control circuit 30 in the video display device 4.

First, the power switch 22 of the endoscope 1 is turned on. After that, when the still image recording changeover switch 24 or the moving image recording changeover switch 25 is turned on, electric power is supplied from the power supply control circuit 30 of the video display device 4 to the LED 16 via the cable 30s. As a result, the LED 16 starts emitting light, and the illumination light emitted from the LED 16 is irradiated from the illumination lens 36, via the light guide bundle 35, to a predetermined range in a direction of region to be inspected 50 in the body cavity.

At this time, heat N is radiated from the LED 16 with the light emission thereof, in the through hole 70b of the illumination means fixing member 70 fixed between the two metal frames 80. Since the LED base 76 and the illumination means fixing member 70 are made of metal member and heat transfer member, respectively, the heat N of the LED 16 radiated in the through hole 70b is transferred, via the LED base 76 and the illumination means fixing member 70, to the suction duct 100 with which a part of the outer circumference of the through hole 70a of the illumination means fixing member 70 (see FIG. 5) comes into close contact.

Then, the suction button 11a is turned on and the suction device connected to the suction base 11 is driven, which allows the fluid such as body fluid or phlegm sucked from inside of the body cavity to be flown in the flow path inside of the suction duct 100. Therefore, the heat N radiated from the LED 16 is absorbed by the fluid flowing in the flow path inside of the suction duct 100 and discharged to the outside of the endoscope 1 together with the fluid from the suction base 11.

That is, the heat N is discharged to the outside of the endoscope 1 from the suction base 11 provided on the rear surface 1h side of the endoscope 1, which is in the direction away from the operator who is at the front surface 1z side of the endoscope 1.

In addition, when the power switch 22 of the endoscope 1 is turned on, the heat N is radiated also from the power supply control circuit 30 with the driving thereof. Since the power supply control circuit 30 is provided in the interior portion 4i occluded by the exterior member 4g of the video display device 4 so as to be located on a rear surface side of the monitor portion 21 observed by the operator, in particular, on the rear surface 4b side of the exterior member 4g, the heat N, as shown in FIG. 9, is discharged in a direction away from the operator, from the rear surface 4b configuring the heat radiation portion away from the operator.

Note that, this is also true when the monitor portion 21 in the video display device 4 is at a position where the display surface of the monitor portion faces upper side which is the insertion axis direction J of the insertion portion 2, or even when the monitor portion 21 is at a position where the display surface thereof faces the front surface 1z side of the endoscope 1 which is the direction P approximately orthogonal to the insertion axis direction J.

Thus, in the present embodiment, when the LED 16 is provided in the space watertightly covered by the exterior member 3g in the grasping portion 8 of the operation portion 3, the illumination means fixing member 70 made of heat transfer member is fixed between the two metal frames 80 fixed to the exterior member 3g. The illumination means fixing member 70 has through holes 70a, 70b formed therein, and the LED 16 is provided in the through hole 70b, and the suction duct 100 is inserted in the through hole 70a.

In addition, the power supply control circuit 30 is provided in the interior portion 4i covered with the exterior member 4g of the video display device 4, and the power supply control circuit 30 is disposed in the interior portion 4i closer to the rear surface 4b side of the exterior member 4g than the monitor portion 21.

With such a configuration, when the LED 16 generates heat with the light emission thereof, the heat N is transmitted to the suction duct 100 through the heat conduction of the illumination means fixing member 70, then radiated, via the suction duct 100, from the suction base 11 provided on the rear surface 1h side of the endoscope 1 away from the operator who is at the front surface 1z side of the endoscope 1. Therefore, the heat N of the LED 16 is surely discharged in the direction avoiding the operator.

In addition, when the power supply control circuit 30 generates heat with the driving thereof, the heat N is radiated from the rear surface 4b of the exterior member 4g of the video display device 4 which is on the rear surface side of the monitor portion 21 to the rear surface 1h side of the endoscope 1. Therefore, the heat N from the power supply control circuit 30 is surely discharged in the direction avoiding the operator who is at the front surface 1z side of the endoscope 1 and observing the monitor portion 21.

Moreover, the LED 16 and the power supply control circuit 30 are provided in the operation portion 3 and the video display device 4, respectively. That is, the LED 16 and the power supply control circuit 30 are provided in positions away from each other in the endoscope 1, so that there are no areas in the endoscope 1 which is locally heated by the heat radiation from the LED 16 and the power supply control circuit 30. That is, dispersion efficiency of the heat N is increased in the endoscope 1, thereby preventing the operator from feeling discomfort by the locally radiated heat N.

Thus, it is possible to provide the endoscope 1 having the configuration in which not only the heat from the light source but also the heat from the power supply control circuit 30 can be surely radiated in a direction other than the direction of the operator who uses the endoscope 1.

Note that a modification example will be shown. FIG. 10 is a cross-sectional view showing a modification example of internal configurations of a part of the operation portion and the video display device.

In the present embodiment, the power supply control circuit 30 is provided on the rear surface side of the monitor portion 21 in the interior portion 4i of the video display device 4.

However, the present invention is not limited to the above, the power supply control circuit 30 may be provided in such a manner as to be fixed to the rear surface 4b of the exterior member 4g in the interior portion 4i, as long as being located on the rear surface side of the monitor portion 21, as shown in FIG. 10.

In this case, since the power supply control circuit 30 is fixed, there is such an inconvenience that the rear surface 4b is heated to become hotter compared with the above embodiment and it is hard for the operator to touch the rear surface 4b. However, except for the inconvenience, the heat N of the power supply control circuit 30 can be radiated from the rear surface 4b in a more proactive manner than in a case of the present embodiment.

In the present embodiment, the LED 16 and the image pickup device 17 are provided in the operation portion 3. However, the present invention is not limited to the same. Even when the LED 16 and the image pickup device 17 are provided in the distal end portion 5 of the insertion portion 2, the same effect as that of the present embodiment can be obtained.

Furthermore, the present embodiment shows an example in which the power supply control circuit 30 and the image pickup device control circuit 33 are separately provided in the video display device 4. However the present invention is not limited to the same, and the power supply control circuit 30 and the image pickup control circuit 33 may be integrally formed. In this case, also the heat N generated with the driving of image pickup device control circuit 33 can be more efficiently discharged from the rear surface 4b side of the exterior member 4g in the direction other than the direction of the operator.

Furthermore, in the present embodiment, the power supply control circuit 30 is provided in the interior portion 4i of the video display device 4. However the present invention is not limited to the same, and the power supply control circuit 30 may be provided in the operation portion 3 or the insertion portion 2.

In this case, if an elongated heat transfer member such as a heat sink is provided in the endoscope 1 so as to be connected from the power supply control circuit 30 in the operation portion 3 or the insertion portion 2 to the rear surface 4b of the video display device 4 by passing through the space 55i of the rotational shaft 55, even in a case where the power supply control circuit 30 is provided in the same place as the LED 16, for example, the heat N of the power supply control circuit 30 is surely discharged, via the elongated heat transfer member, from the rear surface 4b side which is the heat radiation portion of the video display device 4 similarly as in the present embodiment. Therefore, the same effect as that in the present embodiment can be obtained.

In addition, in the present embodiment, the fluid duct is described by taking the suction duct 100 as an example. However, the present invention is not limited to the same. In a case where a duct such as a forward water supply duct through which fluid is flown is extended in the endoscope 1, and an opening of the duct located on a side of the operation portion 3 is oriented in a direction other than the direction of the operator, the heat N radiated from the LED 16 may be transferred to the duct. That is, the heat N radiated from the LED 16 may be transferred to any duct as long as the duct is one, through which fluid is flown, having an opening on the side of the operation portion 3 oriented to a direction other than the direction of the operator.

In addition, though the endoscope 1 is shown taking the medical endoscope as an example in the present embodiment, the similar effect can be obtained even if the present embodiment is applied to an industrial endoscope.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
    an elongated insertion portion inserted into a subject;
    an operation portion provided in a linked manner on a proximal end side of the insertion portion;
    an illumination portion for supplying illumination light for illuminating the subject, the illumination portion being provided in the insertion portion or in the operation portion;
    an image pickup portion for picking up an image of a region to be inspected of the subject, the image pickup portion being provided in the insertion portion or in the operation portion;
    a display device including a display portion on which an endoscope image of the region to be inspected picked up by the image pickup portion is displayed and a frame body for holding the display portion, the display device being connected to the operation portion;
    a light source driving circuit for supplying electric power to drive the illumination portion and cause the illumination portion to emit illumination light, the light source driving circuit being provided on a rear surface side of the display portion in an interior portion enclosed by the display portion and the frame body of the display device; and
    a rear surface, disposed on a surface of the frame body opposing a disposition surface of the frame body on which the display portion in the display device is disposed, configured as a heat conducting portion through which heat generated from the light source driving circuit in the interior portion of the display device transfers from the interior portion side and through which the transferred heat is radiated from an outer surface of the frame body by heat transfer.

2. The endoscope according to claim 1, wherein the light source driving circuit is provided on the rear surface of the frame body in the display device.

3. The endoscope according to claim 1, further comprising,
    recording portion for recording the endoscope image picked up by the image pickup portion, the recording portion being provided in the operation portion or in the display device,
    wherein at least one of a changeover switch for setting the endoscope image to be recorded in the recording portion as a still image or as a moving image, a switch for instructing the recording portion to record the endoscope image, a switch for instructing the display device to display the endoscope image, and a switch for instructing to turning on and off a power of an endoscope main body including the insertion portion, operation portion, and the display device, is provided on the disposition surface of the frame body.

4. The endoscope according to claim 1, wherein a depression is formed on the disposition surface of the frame body, and a display member configuring the display portion and a cover member for covering a display surface of the display member are provided so as to fit in the depression.

5. The endoscope according to claim 1, wherein the display device is connected to the operation portion, by a rotational shaft formed in a connecting portion for connecting the display device with the operation portion, so as to be rotatable between a position where the display portion is oriented in an insertion axis direction of the insertion portion and a position where the display portion is oriented in an direction orthogonal to the insertion axis direction.

6. The endoscope according to claim 5, wherein a cable is inserted in a space inside of the rotational shaft, the cable being extended at least from the light source driving circuit to the illumination portion.

7. The endoscope according to claim 1, wherein the light source driving circuit further comprises an image processing circuit for processing an image such that the endoscope image picked up by the image pickup portion is displayed on the display device.

8. The endoscope according to claim 1, further comprising, in the operation portion:
    an illumination portion disposition space in which the illumination portion is disposed;
    a fluid duct insertion hole through which a part of the fluid duct positioned in the operation portion is inserted, the fluid duct having an opening respectively on a distal end of the insertion portion and the operation portion;
    wherein an illumination portion fixing member, in which at least a part between the illumination portion disposition space and the fluid duct insertion hole is formed of a heat transfer member, is provided.

* * * * *